United States Patent
Hay et al.

(10) Patent No.: US 7,156,329 B2
(45) Date of Patent: Jan. 2, 2007

(54) BONE CRUSHER AND METHOD FOR BONE CRUSHING

(75) Inventors: James Scott Hay, Parkland, FL (US); James Carnation, Tamarac, FL (US); Brian Wieder, Englewood, CO (US); Adrian Panther, Golden, CO (US)

(73) Assignee: Medical Innovators, Inc., Lone Tree, CO (US)

( * ) Notice: Subject to any disclaimer, the term of this patent is extended or adjusted under 35 U.S.C. 154(b) by 0 days.

(21) Appl. No.: 10/961,573

(22) Filed: Oct. 8, 2004

(65) Prior Publication Data
US 2005/0173573 A1   Aug. 11, 2005

Related U.S. Application Data

(60) Provisional application No. 60/542,209, filed on Feb. 5, 2004.

(51) Int. Cl.
*B02C 19/00* (2006.01)

(52) U.S. Cl. .................... 241/30; 241/100; 241/260.1

(58) Field of Classification Search ............ 241/260.1, 241/236, 277, 282, 100, 285.1, 169.1, 243, 241/30
See application file for complete search history.

(56) References Cited

U.S. PATENT DOCUMENTS

| | | | |
|---|---|---|---|
| 1,535,772 A | 4/1925 | Haufier | |
| 2,001,075 A | 5/1935 | Sundstrand | |
| 2,048,509 A | 7/1936 | Melcher et al. | |
| 4,231,527 A | 11/1980 | Bounds | |
| 4,307,846 A | 12/1981 | Spelsberg | |
| 4,715,545 A | 12/1987 | Hanifl et al. | |
| 5,533,683 A | 7/1996 | Fay et al. | |
| 5,607,269 A * | 3/1997 | Dowd et al. | 409/134 |
| 5,769,853 A | 6/1998 | Quetin | |
| 5,791,572 A * | 8/1998 | Fernlund | 241/260.1 |
| 5,918,821 A * | 7/1999 | Grooms et al. | 241/27 |
| 6,287,312 B1 | 9/2001 | Clokie et al. | |
| 6,390,399 B1 | 5/2002 | Mankiewicz | |
| 6,402,070 B1 * | 6/2002 | Ishida et al. | 241/236 |
| 6,464,156 B1 | 10/2002 | Wexell | |
| 6,484,954 B1 | 11/2002 | Lenox | |
| 6,755,365 B1 * | 6/2004 | Meredith | 241/29 |

* cited by examiner

*Primary Examiner*—Mark Rosenbaum
(74) *Attorney, Agent, or Firm*—Christopher & Weisberg, P.A.

(57) ABSTRACT

An apparatus for bone milling includes a housing defining a first opening, a second opening, a third opening, and a linear passage from the first opening to the second opening. The bone mill further includes a rotatable grinding member, wherein the rotatable grinding member has a substantially cylindrical, rod-like shape, with at least a portion of the rotatable grinding member substantially filling or occluding a portion of the linear passage. An actuator element is coupled through the third opening to the rotatable grinding member, and a receptacle is removably coupled to the second opening for retaining the milled material.

18 Claims, 2 Drawing Sheets

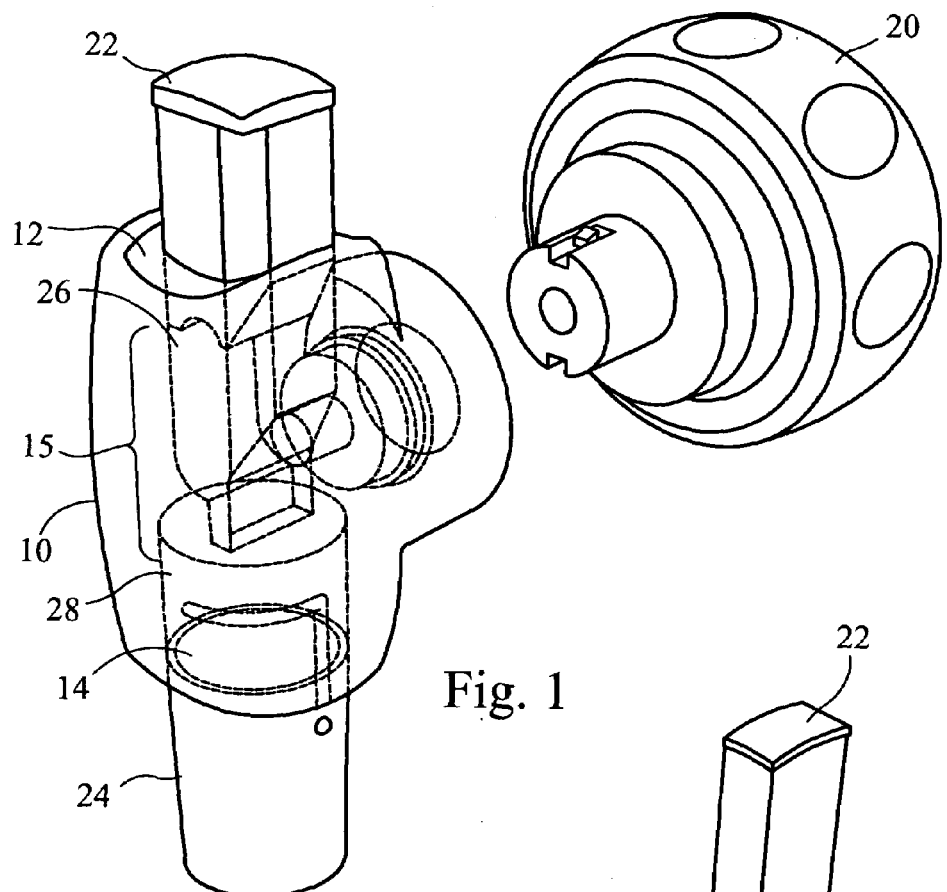
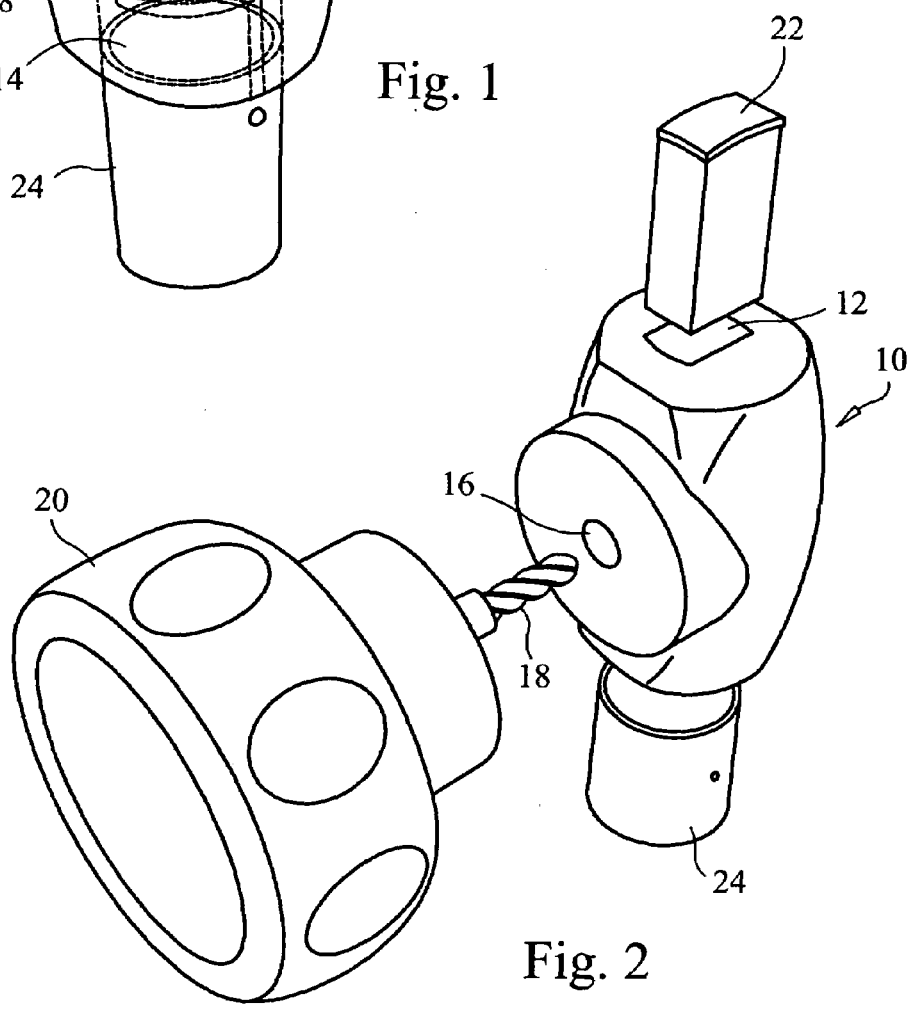

BONE CRUSHER AND METHOD FOR BONE CRUSHING

CROSS-REFERENCE TO RELATED APPLICATION

This application is related to and claims priority to U.S. Provisional Patent Application Ser. No. 60/542,209, filed Feb. 5, 2004, entitled BONE CRUSHER AND METHOD THEREFORE, the entirety of which is incorporated herein by reference.

STATEMENT REGARDING FEDERALLY SPONSORED RESEARCH OR DEVELOPMENT n/a

FIELD OF THE INVENTION

The present invention relates to an orthopedic medical device and method, in particular to a method and device for bone grinding for use during orthopedic surgery.

BACKGROUND OF THE INVENTION

Orthopedic surgery often requires the infusion of a slurry comprised of blood and crushed bone into a surgical site to promote healing and recovery after an injury. The crushed bone in the slurry is ground and pulverized from a larger bone specimen using a bone grinder that reduces the larger specimen into crushed bone particles. Bone mills allow patients to have their own bone particles implanted when there is a preference towards using an autograft to alleviate the possibility of rejection or infection at the surgical site. The surgeon can utilize the bone particles and the resulting slurry to repair bone defects and perform bone augmentation.

Existing bone mills are large, expensive devices which are cumbersome to use and clean and further require re-sterilization at the end of each procedure. Such re-sterilization takes the form of expensive and time consuming gas sterilization or autoclave sterilization. In the case of gas sterilization, the nature of the sterilization process makes the bone mills available for use only once in a 24-hour period. When using an autoclave sterilization process, the bone mills can be sterilized and available for reuse in less than a 24-hour period, however, the bone mills are not immediately available. The resulting period required to re-sterilize the bone mills nevertheless increases the time which necessarily passes between procedures, thereby decreasing operating room and surgical efficiency. Further, the porous nature of blades commonly found in bone mills facilitates the retention of bone particles. The blade porosity hampers the effectiveness of the cleaning process, which furthers the possibility of contamination during subsequent use of the bone mill.

Moreover, existing bone mills are typically powered devices that require an external means for driving the mill, such as a pressurized air source or an electrical motor. Additionally, existing mills may only have the capability to produce a single size of crushed bone particles. As such, a surgical suite needs to have multiple devices to provide crushed bone at different sizes, which greatly increases the cost of having bone-milling capabilities. Otherwise, a surgeon is disadvantageously forced to use crushed bone having a size either too large or too small for a particular surgical procedure, resulting in potential difficulties during an orthopedic procedure.

It is therefore desirable to have an inexpensive bone mill which is easy to sterilize and can further be adapted to create bone chips of different sizes. It is also desirable to have a bone mill which can be manually operated without the assistance of external power sources.

SUMMARY OF THE INVENTION

The present invention advantageously provides a method and system for a bone mill that is easy to sterilize, adapted to create bone chips of different sizes, and operated manually without the need for external power sources. As such, the present invention reduces the overall cost of orthopedic procedures requiring a crushed bone slurry, does not adversely impact the surgical suite turn-over time and provides a high yield of usable bone particles having relatively uniform dimensions.

An exemplary embodiment of the present invention provides a bone mill having a first opening, second opening, and a third opening, with a linear passage extending form the first opening to the second opening. The bone mill also includes a rotatable grinding member which is driven by an actuator element and is preferably hand-driven or operated manually. An exemplary embodiment may further include a plunger for depressing a bone specimen into the linear passage, as well as a receptacle for collecting the milled bone particles.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 illustrates the internal and external features of a bone mill in accordance with the present invention;

FIG. 2 depicts an exploded view of a bone mill in accordance with the present invention.

DETAILED DESCRIPTION OF THE INVENTION

Figure 3:
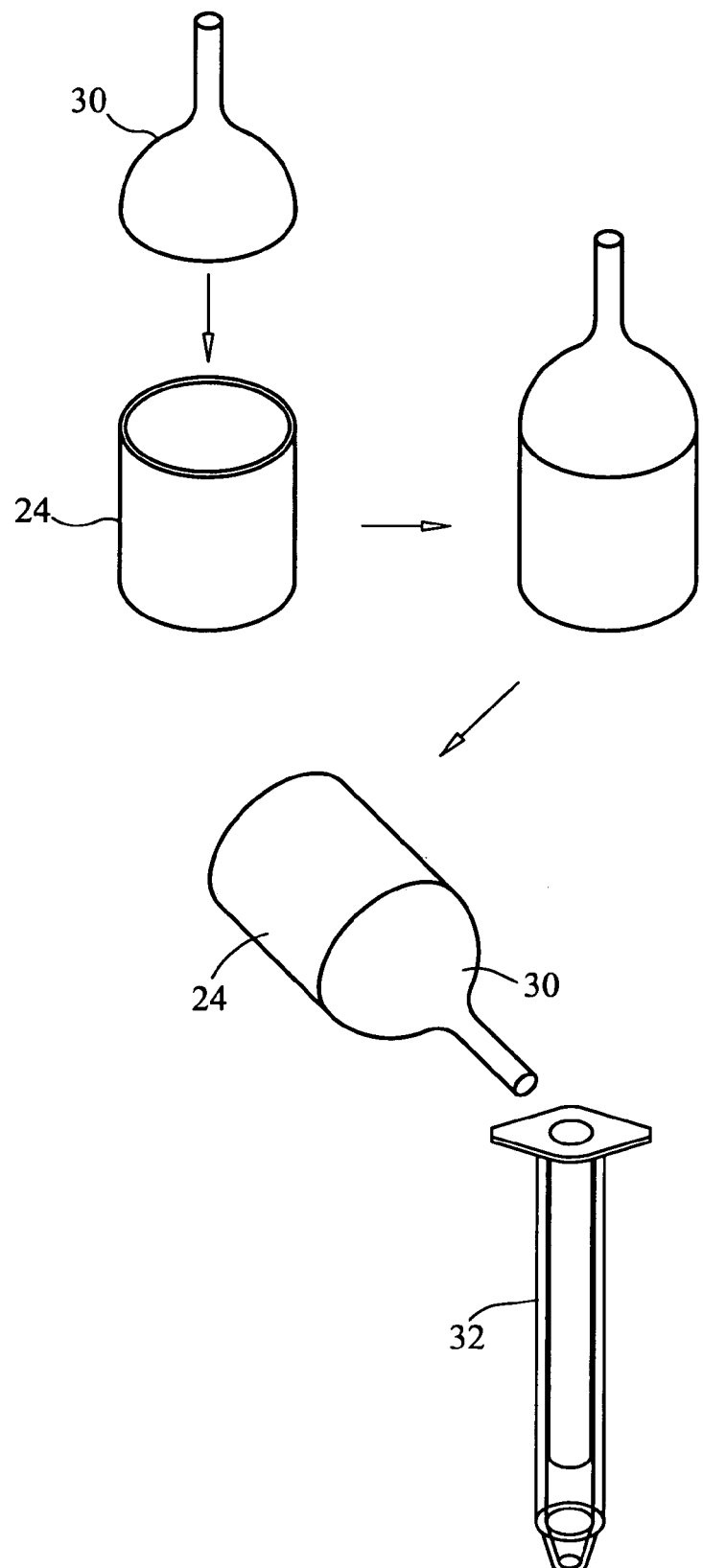
FIG. 3 shows added features of the bone mill in accordance with the present invention.

The present invention provides a disposable, hand-operated bone mill that accommodates cutting plates to produce bone chips of a selected size based on a blade installed in the mill body. Referring now to FIG. 1, an exemplary embodiment of the present invention includes a bone mill having a mill body 10 that defines a first opening 12, a second opening 14, and a linear passage 15 that extends from the first opening 12 to the second opening 14. The mill body 10 further includes a rotatable grinding member 18 coupled to an actuator element 20, as shown in FIG. 2. Further, the mill body 10 can include a third opening 16 through which the rotatable grinding member 18 couples to the actuator element 20. The first opening 12 can be adapted to receive a plunger 22, and a receptacle 24 can be removably coupled to the second opening 14.

The first opening 12 provides an access area into which a suitably sized bone portion can be inserted for milling. First opening 12 can be of any shape, whether having a circular or rectangular cross-section, so long as a bone specimen of a particular dimension can pass through first opening 12 and into the mill body 10 for subsequent milling. First opening 12 can be adapted to receive the plunger 22, which is used to aid in forcing a bone specimen further into the linear passage 15 towards the rotatable grinding member 18. The plunger 22 can be of any shape or orientation, so long as it is capable of being inserted into the first opening 12, and includes at least one depressing surface for contacting a bone specimen in the mill body 10 and forcing it further into the linear passage 15.

The second opening 14 provides an exit area from which milled bone particles may be dispensed. Second opening 14 can be of any shape, whether having a circular or rectangular cross-section, so long as it is of sufficient width to allow milled bone particles to descend out of the opening and into the receptacle 24. Receptacle 24 can be removably coupled to the second opening 14 through any suitable affixation means, including affixation through the use of a threaded interlocking surface, a snap-on mechanism, or the like. Additionally, receptacle 24 may be affixed either to an exterior surface or interior surface of the mill body 10 in the vicinity of the second opening 14 in order to capture the dispensed milled bone material. The receptacle 24 generally defines an interior cavity accessible by a single opening to receive dispensed milled material, and may be of any suitable shape as to be removably coupled to the second opening 24 of the mill body 10.

The rotatable grinding member 18 preferably includes a cylindrical, rod-shaped element having a substantially solid cross-section, and further has at least one cutting element or cutting groove disposed on its outer periphery. Additionally, the rotatable grinding element 18 has a diameter that is less than one-half of an inch, and is positioned in the mill body 10 such that the rotatable grinding member substantially fills or occludes a portion of the linear passage 15. By occluding or filling a portion of the linear passage 15, a bone specimen inserted in the bone mill is ensured direct contact with the rotatable grinding member 18 to further guarantee that only bone chips of a particular dimension proceed further down the linear passageway 15, where they eventually descend into the receptacle 24. An example of a suitable embodiment of the rotatable grinding member 18 is a precision milling bit (for instance, part #233049 from Controx®). The rotatable grinding member is preferably constructed from a highly durable steel or metal material that will not dull easily during repeated uses of the bone mill. Rotatable grinding member 18 can include a spiral-oriented plurality of grooves which present multiple cutting edges for reducing a bone specimen into bone chips or particles. While an exemplary size of the bone particles produced by the rotatable grinding member 18 ranges from one-eighth (⅛) of an inch to approximately three-sixteenths (3/16) of an inch, the measurements and dimensions of the cutting grooves located on the rotatable grinding member may be modified or characterized in order to produce bone chips of an alternatively predetermined size.

Rotatable grinding member 18 is coupled to an actuator element 20 by any suitable means of affixation including a bolt, screw, lock ring, or the like. Actuator element 20 provides the mechanical driving means to rotate the rotatable grinding member 18. The bone mill is preferably manually driven, only requiring the hand strength of a single individual. To ease the use of the bone mill, the actuator element 20 can be in the form of a knob or handle having a diameter or width that is significantly larger than the diameter or width of the rotatable grinding member 18. The size ratio between the actuator element 20 and the rotatable grinding member 18 provides a mechanical advantage for the user and decreases the force that needs to be applied to the actuator element 20 in order to create sufficient force in the rotatable grinding member 18 to successfully reduce a bone specimen into particles of a desired size.

The linear passage 15 provides a direct pathway in which a bone specimen can descend directly through the first opening 12, through the rotatable grinding member 18, and outward from the second opening 14. The linear passage 15 can have any virtually any shape or orientation, whether being a circular or rectangular cross-section, so long as the width is sufficient to receive a bone specimen and allow the specimen to descend through the mill body 10. The linear passage 15 can further include a first region 26 having a first width and a second region 28 having a second width. The first width of the first region 26 can be larger than the second width of the second region 28 so as to accommodate a larger bone specimen, while the second region need only be of sufficient width to allow the milled particles to descend downward to the receptacle 24. Moreover, as is shown in FIG. 1, a portion of the linear passage 15 may be contoured to correspond to a curvature of the rotatable grinding member 18, thereby defining a cutting region disposed between the rotatable grinding member and the contoured portion of the linear passage 15. The rotatable grinding member 18 can be positioned such that at least a portion of the rotatable grinding member 18 intersects at least a portion of the first region 26 and at least a portion of the second region 28 to define the cutting region therebetween. Placing the rotatable grinding member 18 in such a position can ensure that only milled bone particles of a particular size can pass through to the second region 28 and/or the cutting region of the linear passage 15, while maintaining location of the larger bone specimen within the first region 26. Alternatively to having a first and second region, the linear passage can have a single, uniform width, or a plurality of widths, so long as a bone specimen to be milled comes into contact with the rotatable grinding member prior to exiting the mill body 10.

As shown in FIG. 3, the bone mill can further include a funnel 30 and syringe 32. The funnel 30 can be removably coupled to the receptacle 24 when a desired amount of milled bone has been collected. The receptacle 24 is uncoupled from the mill body 10, and is then coupled to the funnel 30 through a mechanism similar to that which coupled the receptacle 24 to the mill body 10, whether by the use of a threaded interlocking surface, a snap-on mechanism, or the like. Upon coupling the receptacle 24 to the funnel 30, the milled contents in the receptacle can be transferred into the syringe 32 for direct insertion to a surgical site. By coupling the funnel 30 directly to the receptacle 24, a user can ensure that no milled contents are wasted or lost when transferring the milled bone from the bone mill to the eventual surgical site.

In an exemplary use prior to a medical procedure, a bone specimen to be milled is inserted into the first opening 12 of the mill body 10. The plunger 22 is then placed into contact with the bone specimen as it resides in the first region 26 of the linear passage 15 in the area above the rotatable grinding member 18. The actuator element 20 is then manually turned, which, in turn, rotates the rotatable grinding member 18. While turning the actuator element 20, the user can depress the plunger, thereby forcing the bone specimen towards and into contact with the rotatable grinding member. As the user continues to depress the plunger and turn the actuator element, the bone specimen will be reduced to bone particles of a desired size, which then descend through the second region 28 of the linear passage 15 and into the receptacle 24 that is removably coupled to the second opening 14 of the mill body.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A hand-operated apparatus for bone milling, comprising:
   a housing defining a first opening, a second opening, and a linear passage from the first opening to the second opening, wherein the linear passage has a first region having a first width and a second region having a second width, the second width being less than half of the first width, and
   a single rotatable grinding member consisting of a single cylindrical, rod-like element having a spiral-oriented plurality of grooves, the rotatable grinding member traversing at least a portion of the linear passage, wherein a portion of the linear passage is contoured to correspond to a curvature of the rotatable grinding member, thereby defining a cutting region disposed between the single rotatable grinding member and the contoured portion of the linear passage, wherein only bone particles of a predetermined size may pass through the cutting region.

2. The apparatus according to claim 1, further comprising an actuator element coupled to the rotatable grinding member.

3. The apparatus according to claim 2, wherein the actuator element is a knob.

4. The apparatus according to claim 3, wherein the knob is circular and has a cross-sectional diameter substantially larger than a cross-sectional diameter of the rotatable grinding member.

5. The apparatus according to claim 2, wherein the housing further defines a third opening through which the rotatable grinding member couples to the actuator element.

6. The apparatus according to claim 1, further comprising a receptacle removably coupled to the second opening.

7. The apparatus according to claim 1, further including a plunger dimensioned to be inserted into the first opening.

8. The apparatus according to claim 1, wherein the first region is adapted to receive a plunger.

9. The apparatus according to claim 1, wherein the second region is adapted to receive a receptacle.

10. The apparatus according to claim 1, wherein at least a portion of the rotatable grinding member intersects at least a portion of the first region and at least a portion of the second region.

11. The apparatus according to claim 1, wherein the rotatable grinding member has a substantially solid cross-section.

12. The apparatus according to claim 1, wherein the rotatable grinding member has a cross-sectional diameter that is less than one-half of an inch.

13. The apparatus according to claim 1, wherein the spiral-oriented plurality of grooves are arranged to produce bone chips of a predetermined size.

14. The apparatus according to claim 1, wherein the housing is constructed from a plastic.

15. A hand-operated apparatus for bone milling, comprising:
    a housing defining a first opening, a second opening, a third opening, and a linear passage from the first opening to the second opening,
    a single rotatable grinding member consisting of a single substantially cylindrical, rod-like shape having a spiral-oriented plurality of grooves and a diameter of less than one-half of an inch, wherein at least a portion of the rotatable grinding member substantially fills or occludes a portion of the linear passage, wherein a portion of the linear passage is contoured to correspond to a curvature of the rotatable grinding member, thereby defining a cutting region disposed between the single rotatable grinding member and the contoured portion of the linear passage, wherein only bone particles of a predetermined size may pass through the cutting region,
    an actuator element coupled through the third opening to the rotatable grinding member, and
    a receptacle removably coupled to the second opening.

16. The apparatus according to claim 15, wherein the rotatable grinding member has a substantially solid core.

17. A hand-operated apparatus for bone milling, comprising:
    a housing defining a first opening, a second opening, a third opening, and a linear passage from the first opening to the second opening, wherein the linear passage has a first region having a first width and a second region having a second width, the first width being greater than the second width,
    a single rotatable grinding member consisting of a single substantially cylindrical, rod-like shape having a cross-sectional diameter of less than one-half of an inch, wherein the rotatable grinding member includes a spiral-oriented plurality of grooves, wherein at least a portion of the rotatable grinding member substantially fills or occludes a portion of the linear passage, wherein a portion of the linear passage is contoured to correspond to a curvature of the rotatable grinding member, thereby defining a cutting region disposed between the single rotatable grinding member and the contoured portion of the linear passage, wherein only bone particles of a predetermined size may pass through the cutting region,
    a circular actuator element coupled through the third opening to the rotatable grinding member, wherein the actuator element has a cross-sectional diameter substantially larger than a cross-sectional diameter of the rotatable grinding member,
    a plunger dimensioned to be inserted into the first opening, and
    a receptacle removably coupled to the second opening.

18. A method for milling bone, comprising the steps of:
    inserting bone to be milled into a hand-operated bone milling apparatus, the apparatus being comprised of a housing defining a first opening for receiving material to be milled, a second opening for dispensing milled material, and a linear passage from the first opening to the second opening, a single rotatable grinding member including a spiral-oriented plurality of grooves, wherein at least a portion of the rotatable grinding member substantially fills or occludes a portion of the linear passage, wherein a portion of the linear passage is contoured to correspond to a curvature of the rotatable grinding member, thereby defining a cutting region disposed between the single rotatable grinding member and the contoured portion of the linear passage, wherein only bone particles of a predetermined size may pass through the cutting region, an actuator element coupled to the rotatable grinding member, a plunger, and a milled material receptacle removably coupled to the second opening, placing the plunger in the first opening of the apparatus to force the bone towards the rotatable grinding member, operating the actuator element to rotate the rotatable grinding member such that the bone is moved between the rotatable grinding member and the housing, thereby milling the bone, and collecting the milled material in the milled material receptacle.

* * * * *